United States Patent [19]

Leanna et al.

[11] Patent Number: 5,712,400
[45] Date of Patent: Jan. 27, 1998

[54] PROCESS FOR PREPARATION OF 5-HYDROXYMETHYLTHIAZOLE

[75] Inventors: M. Robert Leanna, Grayslake; Howard E. Morton, Gurnee, both of Ill.; Michael S. Allen, Silver Lake, Wis.

[73] Assignee: Abbott Laboratories, Abbott Park, Ill.

[21] Appl. No.: 651,439

[22] Filed: May 22, 1996

Related U.S. Application Data

[63] Continuation of Ser. No. 343,690, Nov. 22, 1994, abandoned.

[51] Int. Cl.$^6$ .................... C07D 277/24; C07D 277/22
[52] U.S. Cl. .................................................. 548/202
[58] Field of Search ........................................ 548/202

[56] References Cited

U.S. PATENT DOCUMENTS

| | | | |
|---|---|---|---|
| 4,247,464 | 1/1981 | Relles et al. | 260/326 N |
| 4,748,243 | 5/1988 | Beck et al. | 548/202 |
| 4,822,924 | 4/1989 | Otsu et al. | 568/812 |

FOREIGN PATENT DOCUMENTS

| | | |
|---|---|---|
| 486948 | 2/1992 | European Pat. Off. |
| 9414436 | 7/1994 | WIPO |

OTHER PUBLICATIONS

Von S. Fallab; Helvetica Chimica Acta 215–216 (1952).
South, J. Het. Chem., 28, 1003–11 (1991).
Lee, et al., J. Het. Chem., 22, 1621–30 (1985).
De Selms, Roy C., Org. Prep. Proc. Int. 5(6), 303–304 (1973).
Nozawa, K., et al., Chem. Pharm. Bull., 28(5), 1622–1625, (1980).
March, Jerry, Advanced Organic Chemistry, 4th ed., John Wiley and Sons, p. 398 (1993).
Zahalka et al., Synthesis, 763 (1986).
Noyce, et al., J. Org. Chem. 38, 3316 (1973).

*Primary Examiner*—José G. Dees
*Assistant Examiner*—Laura R. Cross
*Attorney, Agent, or Firm*—Steven R. Crowley

[57] ABSTRACT

A process for the preparation of 5-hydroxymethylthiazole comprises reacting a compound of the formula,

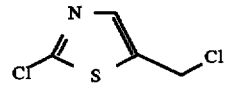

with a carboxylic acid salt (optimally in the presence of a quaternary ammonium salt) and hydrolyzing the resulting ester. Subsequent dechlorination gives 5-hydroxymethylthiazole.

20 Claims, No Drawings

PROCESS FOR PREPARATION OF 5-HYDROXYMETHYLTHIAZOLE

This is a continuation of U.S. patent application Ser. No. 08/343,690, filed Nov. 22, 1994 now abandoned.

TECHNICAL FIELD

The present invention relates to a process and intermediate for the preparation of 5-hydroxymethylthiazole.

BACKGROUND OF THE INVENTION

It has recently been determined that HIV protease inhibiting compounds are useful for inhibiting HIV protease in vitro and in vivo and are useful for inhibiting an HIV (human immunodeficiency virus) infection and are useful for treating AIDS (acquired immunodeficiency syndrome).

It has also recently been determined that compounds of the formula I:

I

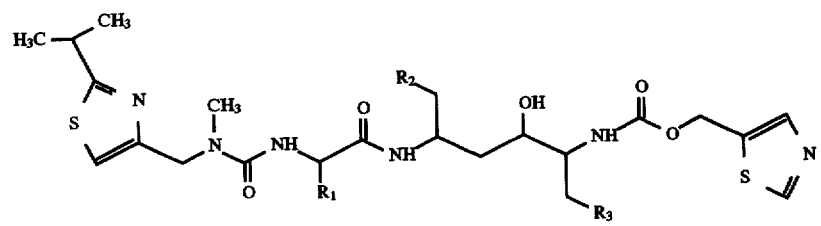

wherein $R_1$ is lower alkyl and $R_2$ and $R_3$ are phenyl are particularly useful as inhibitors of HIV-1 and HIV-2 protease and are useful for inhibiting HIV protease in vitro and in vivo and are useful to inhibit HIV (human immunodeficiency virus) infections and, thus, are useful for the treatment of AIDS (acquired immunodeficiency syndrome).

In particular, the compound of formula II, has been found to be especially effective as an inhibitor of HIV-1 and HIV-2 protease.

II

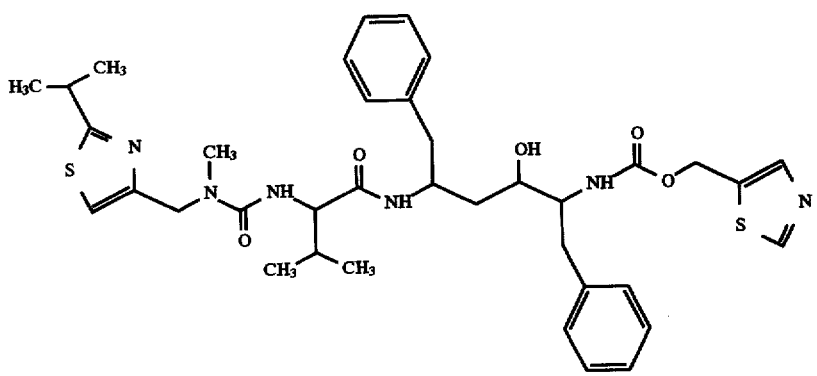

The most preferred compound of formula II is (2S,3S,5S)-5-(N-(N-((N-Methyl-N-((2-isopropyl-4-thiazolyl)methyl) amino)carbonyl)valinyl)amino)-2-(N-((5-thiazolyl) methoxycarbonyl)amino)-1,6-diphenyl-3-hydroxyhexane (compound III).

The preparation of compound III and its use as an inhibitor of HIV protease are disclosed in PCT Patent Application No. WO94/14436, published Jul. 7, 1994, which is hereby incorporated herein by reference.

The term "loweralkyl" as used herein refers to a straight or branched chain alkyl radical containing from 1 to 6 carbon atoms including, but not limited to, methyl, ethyl, n-propyl, iso-propyl, n-butyl, iso-butyl, sec-butyl, t-butyl, n-pentyl, 1-methylbutyl, 2,2-dimethylbutyl, 2-methylpentyl, 2,2-dimethylpropyl, n-hexyl and the like.

A key intermediate in the preparation of compound III is 5-hydroxymethylthiazole.

Methods for the preparation of 5-hydroxymethylthiazole are disclosed in WO94/14436 and include those shown in Scheme 1.

SCHEME 1

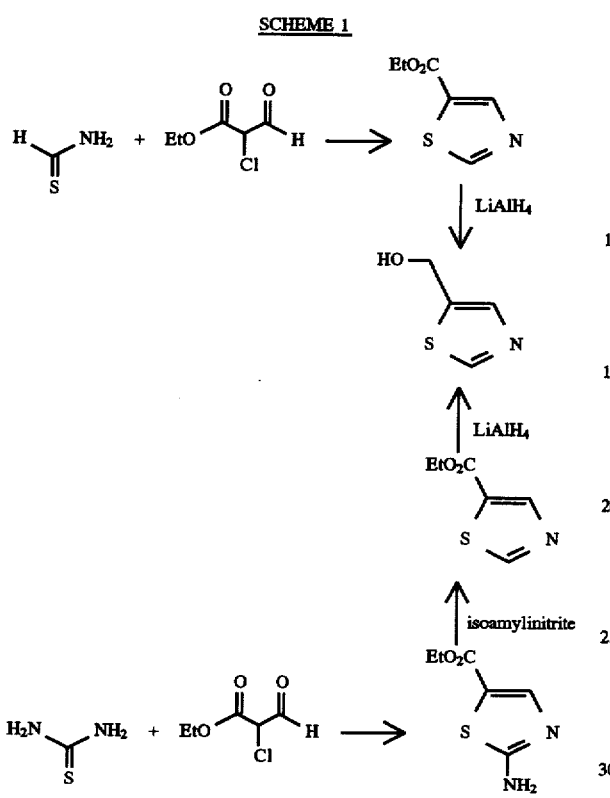

Neither of these methods is suited for large scale production of pure 5-hydroxymethylthiazole. Therefore, there is a continuing need for improved processes for the preparation of 5-hydroxymethylthiazole.

DISCLOSURE OF THE INVENTION

The present invention relates to a process for the preparation of 5-hydroxymethylthiazole:

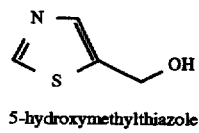

5-hydroxymethylthiazole

The process of this invention (see Scheme 2) comprises a first step of reacting 2-chloro-5-chloromethylthiazole with a carboxylic acid salt (RCOO$^-$ X$^+$ wherein R is hydrogen, loweralkyl or phenyl and X is Na, K, Li or the like) at a temperature of from about 25° C. to about 120° C. to provide an ester of 2-chloro-5-hydroxymethylthiazole. Preferably, the carboxylic acid salt is a formic acid salt (for example, sodium formate, potassium formate or lithium formate and the like). This reaction mixture can further comprise a quaternary ammonium phase transfer catalyst. The reaction can be done in the absence of solvent or a solvent can be used. Suitable solvents include polar aprotic solvents such as dimethylformamide (DMF), dimethylsulfoxide (DMSO), acetonitrile, 1,3-dimethyl-3,4,5,6-tetrahydro-2(1H)-pyrimidone and the like or hydrocarbon solvents such as heptane, octane, decane, benzene, toluene, xylene, cumene and the like.

The ester of 2-chloro-5-hydroxymethylthiazole is hydrolyzed to provide 2-chloro-5-hydroxymethylthiazole. The hydrolysis can be accomplished by adding to the crude reaction mixture resulting from step 1 an ester hydrolyzing agent (for example, trimethylsilyl-OK/tetrahydrofuran and the like or an aqueous solution of a strong base and the like). A preferred ester hydrolyzing agent is an aqueous solution of a strong base (for example, NaOH, KOH or LiOH and the like).

Dechlorination of 2-chloro-5-hydroxymethylthiazole (for example, by catalytic hydrogenation, reaction with zinc/acetic acid or reaction with magnesium/methanol or magnesium/isopropanol and the like) provides 5-hydroxymethylthiazole.

SCHEME 2

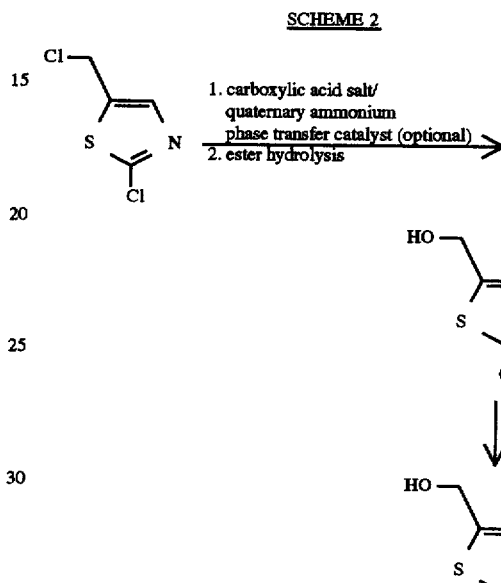

Quaternary ammonium phase transfer catalysts useful in the process of the present invention are disclosed in (1) "Phase-Transfer Catalysis, New chemistry, Catalysts and Applications", ACS Symposium Series 326, American Chemical Society, Wash., D.C., 1987, Charles M. Starks (editor), (2) "Phase-Transfer Reactions", Fluka-Compendium, Volume 1, Georg Thieme Verlag, New York, 1986, Walter E. Keller (editor) and (3) "Phase-Transfer Reactions", Fluka-Compendium, Volume 2, Georg Thieme Verlag, New York, 1987, Walter E. Keller (editor), all three of which are hereby incorporated herein by reference. Suitable quaternary ammonium phase transfer catalysts include, but are not intended to be limited to, butylpyridinium bromide, benzyltriethylammonium bromide, benzyltriethylammonium chloride, benzyltrimethylammonium chloride, benzyltrimethylammonium fluoride, hexadecyltriethylammonium bromide, hexadecyltrimethylammonium bromide, hexadecyltrimethylammonium chloride, dibutyldimethylammonium chloride, decyltriethylammonium bromide, heptylpyridinium bromide, hexyltriethylammonium bromide, dodecylpyridinium bromide, dodecyltriethylammonium bromide, methyltrinonylammonium chloride, methyltriphenylammonium bromide, octyltriethylammonium bromide, tetrabutylammonium bromide, tetrabutylammonium chloride, tetrabutylammonium iodide, tetrabutylammonium hydroxide, tetraethylammonium chloride, tetramethylammonium bromide, tricaprylylmethyl ammonium chloride, trioctylmethylammonium chloride, trioctylpropylammonium chloride, tetrapropylammonium bromide, or the like.

The starting material, 2-chloro-5-chloromethylthiazole, can be prepared as described in U.S. Pat. No. 4,748,243.

In the process of the invention, the formic acid salt (or other like carboxylic acid salts) is used in an amount of from about 1.0 to about 5.0 mole equivalents (based on 2-chloro-5-chloromethylthiazole), preferably from about 2.5 to about 3.5 mole equivalents.

When present, the quaternary ammonium phase transfer catalyst is used in an amount from about 0.01 to about 0.1 mole equivalents (based on 2-chloro-5-chloromethylthiazole), preferably from about 0.01 to about 0.02 mole equivalents.

When ester hydrolysis is accomplished with aqueous strong base, the aqueous strong base comprises from about 1.0 to about 2.0 mole equivalents (based on 2-chloro-5-chloromethylthiazole) of the strong base (preferably, from about 1.0 to about 1.2 mole equivalents) at a concentration of from about 5% to about 50%, preferably from about 20% to about 30% (w/w).

Catalytic hydrogenation is a preferred method for dechlorination. The catalytic hydrogenation of 2-chloro-5-hydroxymethylthiazole can be accomplished using hydrogen at a pressure of from about 1 atmosphere to about 10 atmospheres, and a hydrogenation catalyst (e.g., Pd/C, RaNi, and the like) in the amount of from about 1% to about 25% (by weight) in an inert solvent (e.g., methanol, ethanol, and the like).

The foregoing may be better understood by reference to the following examples which are provided for illustration and are not intended to limit the scope of the inventive concept.

EXAMPLE 1

A. Preparation of 2-chloro-5-hydroxymethylthiazole

A 10.56 gram (gm) sample of 2-chloro-5-chloromethylthiazole (62.85 millimoles (mmol)) was placed in a 50 milliliter (mL) reaction flask. Added to the reaction flask were 12.82 gm (188 mmol) of sodium formate and 0.5 gm (1.2 mmol) of tricaprylylmethyl ammonium chloride and the mixture was heated and stirred at 80° C. for 8.5 hours (hr). A magnetic stir bar was used to stir the mixture and the sides of the reaction flask were washed every 1.5 hr with 1–2 ml of diethyl ether. The top of the reaction flask was removed for about 1 minute to allow the ether to evaporate out of the mixture.

The reaction flask was cooled to 5° C. and a 25% aqueous solution of NaOH (5.53 gm of a 50% NaOH solution diluted with 5.5 gm of ice) was added dropwise to the reaction flask with stirring for approximately 15 minutes.

The reaction mixture was diluted with 70 mL of methyl-t-butyl-ether, 25 mL of water, and 5 mL of an aqueous saturated sodium chloride (NaCl) solution. The diluted reaction mixture was transferred to a separatory funnel where it formed separate layers. The aqueous layer was separated and washed with 25 mL of methyl-t-butyl ether, which was then recombined with the organic layer. The organic layer was dried over sodium sulfate ($Na_2SO_4$). Added to this was 1 gm of activated charcoal (Darco® 60) and 2 gm of silica gel and swirled for 2 minutes. The resulting mixture was filtered through a diatomaceous earth pad in a 30 mL coarse sintered glass funnel. The diatomaceous earth pad was washed 5 times with 10 mL of methyl-t-butyl ether to remove any final product from the pad. The resultant product was concentrated in a vacuum to yield 9.45 gm of 5-hydroxymethyl-2-chlorothiazole. $^1$H NMR ($CDCl_3$) δ7.41 (s, 1H), 4.81 (s,2H), 2.40 (bs, 1H). MS(Cl) m/e 150/152 $(M+H)^+$, 167/169 $(M+NH_4)^+$.

B. Alternative Preparation of 2-chloro-5-hydroxymethylthiazole

To a 3 necked 1 liter round bottom flask equipped with an overhead stirrer was charged 2-chloro-5-chloromethyl thiazole (100.0 g, 0.6 mole), sodium formate (121.5 g, 1.8 mole, 3 eq), tricaprylylmethyl ammonium chloride (4.81 g, 11.9 mmol, 0.02 eq.) and heptane (125 mL). The mixture which resulted was heated to 85° C. with slow stirring. The reaction was allowed to stir overnight after which time the mixture was cooled to room temperature and quenched with a 25% aqueous solution of sodium hydroxide (100 g of 50% aq. NaOH, 100 g of ice), not letting the internal temperature of the quenched mixture exceed 25° C. The reaction mixture was then stirred for 30 minutes and then diluted with $H_2O$ (100 mL), 20% aq. NaCl (100 mL) and methyl t-butyl ether (200 mL). Stirring continued for an additional 15 minutes. After settling, the layers were separated and the lower aqueous layer was re-extracted with methyl t-butyl ether (2×200 mL). The combined organic extracts were dried over sodium sulfate (75 g) and filtered. To this filtrate was charged Darco G-60 carbon (9.47 g) and silica gel 230–400 mesh (18.9 g). This suspension was stirred at room temperature for 30 minutes and then filtered through a bed of diatomaceous earth. Methyl t-butyl ether (5×20 mL) was used as a flask and filter cake rinse. The combined filtrates were concentrated under reduced pressure (42° C.) until constant weight was achieved. 2-chloro-5-hydroxymethyl thiazole was thus isolated as a light yellow colored oil (84.0 g, 94.4%). $^{13}$C NMR (CDCl3) (ppm) 57, 138, 141, 152.

C. Preparation of 5-Hydroxymethylthiazole

A 2.04 gm (13.64 mmol) sample of 5-hydroxymethyl-2-chlorothiazole was dissolved in 25 mL of methanol. The dissolved sample was placed in a Parr shaker which was charged with sodium acetate.3 $H_2O$ (1.1 mole equivalents) and 200 milligrams (mg) of 10% palladium/carbon. The system was charged with 4 atmospheres of $H_2$ gas and heated at 60° C. with shaking for 18–24 hr. The shaker was cooled, the reaction mixture was filtered and the filtrate was concentrated in a vacuum. The concentrate was slurried with 50 mL of methyl-t-butyl ether and subsequently dried over $Na_2SO_4$. The dried solution was concentrated in a vacuum and 1.74 gm of a clear oil was obtained. 1.24 gm of the oil was chromatographed onto 15 gm of silicon dioxide ($SiO_2$). The oil was eluted with 100% ethylacetate. The eluates were combined and concentrated under vacuum to provide 1.02 gm of 5-hydroxymethylthiazole as an oil. $^1$H NMR ($CDCl_3$) δ8.76 (s, 1H), 7.75 (d,1H), 4.92 (s, 2H), 2.88 (bs, 1H). MS(Cl) m/e 116 $(M+H)^+$, 133 $(M+NH_4)^+$.

D. Alternative Preparation of 5-Hydroxymethylthiazole

2-Chloro-5-hydroxymethylthiazole (74.0 g, 495 mmol), was dissolved in methanol (925 mL) and charged into a Parr Shaker. To this solution was charged sodium carbonate (26.76 g, 252.5 mmol, 0.51 eq) and 10% palladium on carbon (11.1 g). The system was heated (60° C.) under 50 psi (3.40 atm) of hydrogen gas and agitated for 8 hours. (The reaction mixture can be vented periodically to release the buildup of carbon dioxide gas). The shaker was then cooled and the contents filtered through a bed of diatomaceous earth. The filtrate was then concentrated under reduced pressure (38° C.) and the residue which resulted was taken up in methyl t-butyl ether (600 mL) and dried over sodium sulfate (70 g). This dried solution was then filtered and concentrated under reduced pressure (38° C.) to provide 5-hydroxymethylthiazole 52.2 g, 91.6%.

The foregoing is merely illustrative of the invention and is not intended to limit the invention to the disclosed processes and reaction conditions. Variations which are obvious to one of ordinary skill in the art are intended to be included within the scope and nature of the invention which are defined in the appended claims.

We claim:

1. A process for preparing 5-hydroxymethylthiazole comprising:
   (a) reacting 2-chloro-5-chloromethylthiazole with a carboxylic acid salt;
   (b) reacting the resulting product of step (a) with an ester hydrolyzing agent; and
   (c) dechlorinating the product of step (b).

2. The process of claim 1 further comprising in step (a) a quaternary ammonium phase transfer catalyst.

3. The process of claim 1 wherein the dechlorination is accomplished by catalytic hydrogenation or reaction with zinc/acetic acid.

4. A process for preparing 5-hydroxymethylthiazole comprising:
   (a) reacting 2-chloro-5-chloromethylthiazole with a formic acid salt in the presence of a quaternary ammonium phase transfer catalyst;
   (b) reacting the resulting product of step (a) with an aqueous solution of strong base; and
   (c) dechlorinating the product of step (b).

5. The process of claim 4 wherein the formic acid salt is sodium formate, potassium formate or lithium formate.

6. The process of claim 4 wherein the quaternary ammonium phase transfer catalyst is tricaprylylmethyl ammonium chloride.

7. The process of claim 4 wherein the dechlorination is accomplished by catalytic hydrogenation or reaction with zinc/acetic acid.

8. A process for preparing 5-hydroxymethylthiazole comprising
   (a) reacting 2-chloro-5-chloromethylthiazole with a formic acid salt in the presence of tricaprylylmethyl-ammonium chloride;
   (b) reacting the resulting product of step (a) with aqueous sodium hydroxide; and
   (c) catalytic hydrogenation of the product of step (b).

9. A process for preparing 2-chloro-5-hydroxymethylthiazole comprising:
   (a) reacting 2-chloro-5-chloromethylthiazole with a formic acid salt in the presence of a quaternary ammonium phase transfer catalyst; and
   (b) reacting the resulting product of step (a) with an aqueous solution of strong base.

10. The process of claim 9 wherein the formic acid salt is sodium formate and the quaternary ammonium phase transfer catalyst is tricaprylylmethyl ammonium chloride.

11. A process for preparing 5-hydroxymethylthiazole comprising:
    (a) reacting 2-chloro-5-chloromethylthiazole with a carboxylic acid salt;
    (b) reacting the resulting product of step (a) with an ester hydrolyzing agent to provide a product which comprises greater than about 94% of 2-chloro-5-hydroxymethylthiazole; and
    (c) dechlorinating the product of step (b).

12. The process of claim 11 further comprising in step (a) a quaternary ammonium phase transfer catalyst.

13. The process of claim 11 wherein the dechlorination is accomplished by catalytic hydrogenation or reaction with zinc/acetic acid.

14. A process for preparing 5-hydroxymethylthiazole comprising:
    (a) reacting 2-chloro-5-chloromethylthiazole with a formic acid salt in the presence of a quaternary ammonium phase transfer catalyst;
    (b) reacting the resulting product of step (a) with an aqueous solution of strong base to provide a product which comprises greater than about 94% of 2-chloro-5-hydroxymethylthiazole; and
    (c) dechlorinating the product of step (b).

15. The process of claim 14 wherein the formic acid salt is sodium formate, potassium formate or lithium formate.

16. The process of claim 14 wherein the quaternary ammonium phase transfer catalyst is tricaprylylmethyl ammonium chloride.

17. The process of claim 14 wherein the dechlorination is accomplished by catalytic hydrogenation or reaction with zinc/acetic acid.

18. A process for preparing 5-hydroxymethylthiazole comprising
    (a) reacting 2-chloro-5-chloromethylthiazole with a formic acid salt in the presence of tricaprylylmethyl-ammonium chloride;
    (b) reacting the resulting product of step (a) with aqueous sodium hydroxide to provide a product which comprises greater than about 94% of 2-chloro-5-hydroxymethylthiazole; and
    (c) catalytic hydrogenation of the product of step (b).

19. A process for preparing 2-chloro-5-hydroxymethylthiazole comprising:
    (a) reacting 2-chloro-5-chloromethylthiazole with a formic acid salt in the presence of a quaternary ammonium phase transfer catalyst; and
    (b) reacting the resulting product of step (a) with an aqueous solution of strong base to provide a product which comprises greater than about 94% of 2-chloro-5-hydroxymethylthiazole.

20. The process of claim 19 wherein the formic acid salt is sodium formate and the quaternary ammonium phase transfer catalyst is tricaprylylmethyl ammonium chloride.

* * * * *